United States Patent [19]
Miyake et al.

[11] Patent Number: 5,922,712
[45] Date of Patent: Jul. 13, 1999

[54] EOSINOPHIL CHEMOTAXIS INHIBITOR

[75] Inventors: Akio Miyake; Yasuko Ashida; Tatsumi Matsumoto, all of Osaka, Japan

[73] Assignee: Takeda Chemical Industries, Ltd., Osaka, Japan

[21] Appl. No.: 09/070,928

[22] Filed: May 1, 1998

Related U.S. Application Data

[62] Division of application No. 08/692,644, Aug. 6, 1996, abandoned, which is a continuation of application No. 08/308,501, Sep. 21, 1994, abandoned.

[30] Foreign Application Priority Data

Sep. 21, 1993 [JP] Japan ..................................... 5-234764

[51] Int. Cl.$^6$ .................................................. A61K 31/50
[52] U.S. Cl. .......................................................... 514/248
[58] Field of Search ............................................ 514/248

[56] References Cited

U.S. PATENT DOCUMENTS 5,011,835  4/1991  Peet et al. ................................. 514/748
5,039,689  8/1991  Daluge ..................................... 514/748

FOREIGN PATENT DOCUMENTS

| | | |
|---|---|---|
| 0 381 132 | 8/1990 | European Pat. Off. . |
| 0 440 119 | 8/1991 | European Pat. Off. . |
| 0 444 549 | 9/1991 | European Pat. Off. . |
| 0 548 923 | 6/1993 | European Pat. Off. . |
| 0 562 439 | 9/1993 | European Pat. Off. . |
| 0 562 440 | 9/1993 | European Pat. Off. . |

OTHER PUBLICATIONS

Berkow et al., "The Merck Manual" *Merck Research Laboratories*, USA 16th edition, chapter 98, pp. 1230–1231 (1992).

Labrakis–Lazanas, Katerina et al., "PAF of Biological Fluids in Disease: Blood Levels in Allergic Rhinitis" vol. 73, pp. 379–382; *Haematologica* (1998).

Chemical Abstract AN 93–153853, Korth, to EP 540766, (1993).

Chemical Abstracts, AN 1990:629449 Misawa et al., (1990).

Chemical Abstracts, AN 1990:214771 Fukuda et al., (1990).

*Primary Examiner*—Phyllis G. Spivack
*Attorney, Agent, or Firm*—Foley & Lardner

[57] ABSTRACT

A method for inhibiting eosinophil infiltration by administrating to a subject in need thereof an effective amount of a compound of the formula:

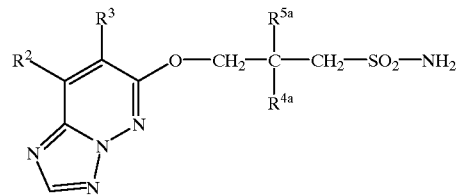

wherein $R^2$ and $R^3$ independently represent a hydrogen atom or a $C_{1-4}$ group, and $R^{4a}$ and $R^{5a}$ independently represent a hydrogen atom or a $C_{1-4}$ alkyl group, or a pharmaceutically acceptable salt thereof.

4 Claims, No Drawings

EOSINOPHIL CHEMOTAXIS INHIBITOR

This application is a divisional of application Ser. No. 08/692,644, filed Aug. 6, 1996 abandoned, which is a continuation of application Ser. No. 08/308,501 filed Sep. 21, 1994, abandoned.

This invention relates to an eosinophil chemotaxis inhibitor composition and a pharmaceutical composition for the treatment of diseases involving eosinophilic infiltration or eosinophilia, such as allergic rhinitis, atopic dermatitis, etc., each comprising a condensed pyridazine derivative or a salt thereof.

In allergic diseases, various chemical mediators such as leukotrienes $B_4$, $C_4$ and $D_4$, prostaglandins $E_2$, $F_{2\alpha}$ and $I_2$, thromboxane $A_2$, platelet activating factor (PAF), histamine, heparin, serotonin, allyl sulfatase, neutrophil chemotactic factor (NCF), eosinophil chemotactic factor (ECF-A), etc. are released from mast cells at the local sites of reaction to cause allergic responses. These allergic responses can be controlled by inhibiting the release of such chemical mediators or antagonizing their actions. These chemical mediators further trigger the chemotaxis of eosinophils, neutrophils, lymphocytes, monocytes and macrophages and induce allergic responses of the infiltrated cells. The eosinophils, in particular, reach high levels in the circulating blood and nasal discharge and G. J. Gleich and coworkers "J. Allergy Clin. Immunol. 80, 412–415, 1987" report that eosinophilic infiltration is involved in a great measure in atopic dermatitis, allergic rhinitis and other allergic diseases. Furthermore, an elevation of eosinophil count is found in parasitogenic diseases and eosinophilia and it is not true that all antiallergic agents inhibit eosinophil infiltration.

Meanwhile, EP-A-381132, EP-A-440119 and EP-A-444549, among others, describe compounds each consisting of an imidazopyridazine skeleton and a side chain attached to the skeleton through a hetero-atom and EP-A-548923, for instance, describes compounds each consisting of an imidazopyridazine and triazolopyridazine skeleton and a side chain attached to the skeleton through a carbon atom. These compounds are known to have antiinflammatory and antiallergic properties based on anti-PAF activity and, as such, may be of value as antiasthmatic agents but there is no reference to inhibition of eosinophil infiltration.

There has been a standing need to this day for a new eosinophil chemotaxis inhibitor, a therapeutic agent for allergic rhinitis and a therapeutic agent for atopic dermatitis, each of which would show inhibitory activity against eosinophil infiltration, that is to say an inhibitory effect on the chemotaxis of eosinophils, and no potential of causing adverse reactions.

For the purpose of solving the above problems, the inventors of this invention explored in earnest for compounds having eosinophil chemotaxis inhibitory activity and discovered that condensed pyridazine derivatives including the following specific and partial chemical structure:

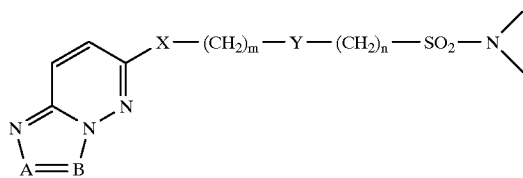

wherein the symbols have the same meanings defined hereinafter have unexpectedly high eosinophil chemotaxis inhibitory activity and are of value for the treatment of diseases involving eosinophil infiltration or eosenophilia such as allergic rhinitis and atopic dermatitis. This invention has been developed on the basis of the above findings.

This invention is accordingly directed to (1) A composition for inhibiting an eosinophil chemotaxis which comprises a compound of the formula:

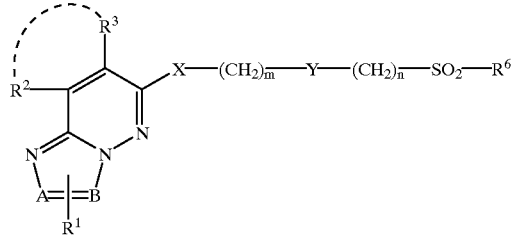

wherein $R^1$ represents a hydrogen atom, an optionally substituted lower alkyl group or a halogen atom; either A or B represents a nitrogen atom with the other representing a methine group, or both of them represent a methine group;

$R^2$ and $R^3$ independently represent a hydrogen atom or an optionally substituted lower alkyl group, or $R^2$ and $R^3$ taken together with the adjacent —C=C—, may form a 5- to 7-membered ring;

X represents a methylene group, an oxygen atom or S(O)p wherein p represents an integer of 0 to 2;

Y represents (i) a group of the formula:

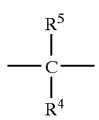

wherein $R^4$ and $R^5$ independently represent a hydrogen atom or an optionally substituted lower alkyl group or (ii) a divalent group derived from an optinally substituted 3- to 7-membered homocyclic or heterocyclic ring;

$R^6$ represents a primary to tertiary amino group; m and n independently represent an integer of 0 to 4, or a salt thereof, (2) a composition as described above in (1), wherein $R^1$ represents a hydrogen atom.

(3) a composition as described above in (1), wherein $R^2$ and $R^3$ independently represent a hydrogen atom or a $C_{1-4}$ alkyl group, (4) a composition as described above in (1), wherein X represents an oxygen atom or a sulfur atom, (5) a composition as described above in (1), wherein A and B each represent a methine group, (6) a composition as described above in (1), wherein A represents a methine group and B represents a nitrogen atom, (7) a composition as described above in (1), wherein Y represents a group of the formula

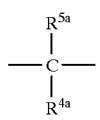

wherein $R^{4a}$ and $R^{5a}$ independently represent a hydrogen atom or a $C_{1-4}$ akyl group, (8) a composition as described above in (1), wherein Y represents a $C_{3-7}$ cycloalkylidene group, (9) a composition as described above in (1), wherein $R^6$ represents (i) an amino group which may be substituted by 1 or 2 substituents selected from the group consisting of an optionally substituted lower alkyl group, an optionally substituted cycloalkyl group and an optionally substituted aryl group or (ii) an optionally substituted cyclic amino group,

(10) a composition as described above in (1), wherein $R^6$ represents (1) a group of the formula:

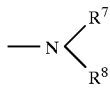

wherein $R^7$ and $R^8$ independently represent (i) a hydrogen atom, (ii) a $C_{1-6}$ alkyl group which may be substituted by a pyrrolyl, imidazolyl, pyridyl or pyrimidyl group which may be substituted by a $C_{1-4}$ alkyl group or (iii) a $C_{3-6}$ cycloalkyl group or (2) a group of the formula:

wherein $R^9$ represents a hydrogen atom, a $C_{1-6}$ alkyl group, a pyrrolyl group, an imidazolyl group, a pyridyl group or a pyrimidyl group,

(11) a composition as described above in (1), wherein $R^6$ represents an amino group,

(12) a composition as described above in (1), wherein $R^1$ represents (i) a hydrogen atom, (ii) a $C_{1-6}$ alkyl group which may be substituted with one or two substituents selected from the group consisting of a hydroxy, amino, carboxyl, nitro, mono- or di-$C_{1-6}$ alkylamino, $C_{1-6}$ alkoxy, $C_{1-6}$ alkyl-carbonyloxy, phenyl and halogen or (iii) a halogen atom;

A represents a methine group;

B represents a nitrogen atom;

$R^2$ and $R^3$ independently represent a hydrogen atom or a $C_{1-6}$ alkyl group which may be substituted with one or two substituents selected from the group consisting of a hydroxy, amino, carboxyl, nitro, mono- or di-$C_{1-6}$ alkylamino, $C_{1-6}$ alkoxy, $C_{1-6}$ alkyl-carbonyloxy, phenyl and halogen;

X stands for an oxygen atom or $S(O)_p$ wherein p is an integer of 0 to 2;

Y stands for (1) a group of the formula:

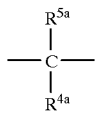

wherein $R^{4a}$ and $R^{5a}$ independently represent a hydrogen atom or a $C_{1-4}$ alkyl group or (2) a divalent 3- to 7-membered homocyclic ring selected from the group consisting of

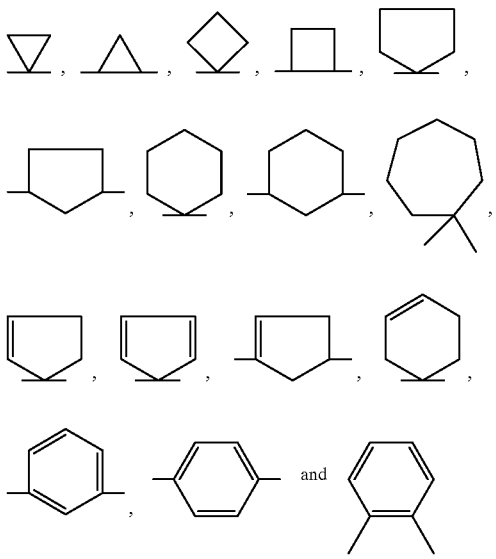

which each may be substituted with 1 to 5 substituents selected from the group consisting of (i) a $C_{1-6}$ alkyl group, (ii) a mono- or di-$C_{1-4}$ alkylamino group, (iii) a hydroxy group, (iv) a carboxyl group, (v) a nitro group, (vi) a $C_{1-6}$ alkoxy group, (vii) a pyrrolyl, imidazolyl, pyridyl or pyrimidyl group which may be substituted by one to four $C_{1-4}$ alkyl group, and (viii) a halogen;

$R^6$ represents (1) a group of the formula:

wherein $R^7$ and $R^8$ independently represent (i) a hydrogen atom, (ii) a $C_{1-6}$ alkyl group which may be substituted with one pyrrolyl, imidazolyl, pyridyl or pyrimidyl group which may be substituted by one $C_{1-4}$ alkyl group or (iii) a $C_{3-6}$ cycloalkyl group, or (2) a group of the formula:

wherein $R^9$ represents a hydrogen atom, a $C_{1-6}$ alkyl group, a pyrrolyl group, an imidazolyl group, a pyridyl group or a pyrimidyl group;

m stands for an integer of 0 to 4; and n stands for an integer of 0 to 4,

(13) a composition as described above in (1), wherein $R^1$ represents a hydrogen atom, $R^2$ represents a hydrogen atom, R represents a $C_{1-6}$ alkyl group, A represents a methylene group, B represents a nitrogen atom, X represents an oxygen atom, Y represents a group of the formula

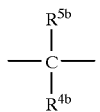

wherein $R^{4b}$ and $R^{5b}$ independently represent a $C_{1-4}$ alkyl group, $R^6$ represents an amino group, m represents 1 and n represents an integer of 1 to 4,

(14) a composition as described above in (1), which is for the treatment of a disease involving eosinophilia.

(15) a composition as described above in (14), which the disease is an allergic rhinitis,

(16) a composition as described above in (14), which the disease is an atopic dermatitis, and so on.

It should be understood that where the compound (I) or a salt thereof contains asymmetric carbon within its structure, it may occur as optically active forms as well as racemic mixtures and that such respective isomers and mixtures of isomers also fall within the scope of this invention.

As used throughout this specification, the term "lower alkyl" generally means, for example, a straight-chain or brached $C_{1-6}$ alkyl group. The $C_{1-6}$ alkyl group includes methyl, ethyl, n-propyl, i-propyl, n-butyl, i-butyl, tert-butyl, n-pentyl, n-hexyl, etc. Preferred, among them, are $C_{1-4}$ alkyl groups such as methyl, ethyl, n-propyl and i-propyl, etc.

The term "cycloalkyl" generally means, for example, a $C_{3-6}$ cycloalkyl group. The $C_{3-6}$ cycloalkyl group includes cyclopropyl, cyclobutyl, cyclopentyl, cyclohexyl, etc.

The term "aryl" generally means, for example, a $C_{6-14}$ aryl group. The $C_{6-14}$ aryl group includes phenyl, naphthyl, etc. and is preferably phenyl.

The substituent group by which said "lower alkyl" and "cycloalkyl" may be substituted includes hydroxy, amino, carboxyl, nitro, mono- or di-lower alkylamino (e.g. mono- or di-$C_{1-6}$ alkylamino such as methylamino, ethylamino, propylamino, dimethylamino, diethylamino, etc.), lower alkoxy (e.g. $C_{1-6}$ alkoxy such as methoxy, ethoxy, propoxy, hexyloxy, etc.), lower alkylcarbonyloxy (e.g. $C_{1-6}$ alkyl-carbonyloxy such as acetoxy, ethylcarbonyloxy, etc.), phenyl, and halogen (e.g. fluorine, chlorine, bromine, iodine, etc.). These substituents may substitute on the lower alkyl group or cycloalkyl group at any possible position, and two or more of such substituents may be the same or different. The number of these substituents is, for example, about 1 to 4, preferably 1 or 2. And, the "lower alkyl" may have an optionally substituted heterocyclic group as described hereinafter.

The term "heterocyclic group" may be a 5- to 7-membered nitrogen-containing heterocyclic group consisting of 1 or 2 nitrogen atoms and the remainder of carbon atoms, such as pyrrolyl, imidazolyl, pyridyl, pyrimidyl, etc., and these heterocyclic groups may respectively have 1 to 4 substituent groups selected from hydroxy, amino, carboxyl, nitro, mono- or di-lower alkylamino (e.g. mono- or di-$C_{1-6}$ alkylamino such as methylamino, ethylamino, propylamino, dimethylamino, diethylamino, etc.), lower alkoxy (e.g. $C_{1-6}$ alkoxy such as methoxy, ethoxy, propoxy, hexyloxy, etc.), lower alkyl-carbonyloxy (e.g. $C_{1-6}$ alkyl-carbonyloxy such as acetoxy, ethylcarbonyloxy, etc.), phenyl, halogen (e.g. fluorine, chlorine, bromine, iodine, etc.) and $C_{1-6}$ alkyl (e.g. methyl, ethyl, n-propyl, i-propyl, n-butyl, i-butyl, tert-butyl, etc.). Particularly preferred substituent groups are a $C_{1-4}$ alkyl group (e.g. methyl, ethyl, n-propyl, i-propyl, etc.).

The substituent group by which said "aryl" group may be substituted includes an optionally substituted lower alkyl, an optionally substituted amino, a 5- to 7-membered cycloamino (e.g. pyrrolidino, morpholino, piperidino, piperazino, etc.), an optionally substituted amido, hydroxy, carboxy, nitro, lower alkoxy (e.g. $C_{1-6}$ alkoxy such as methoxy, ethoxy, propoxy, etc.), lower alkylcarbonyloxy (e.g. $C_{1-6}$ alkyl-carbonyloxy such as acetoxy, ethylcarbonyloxy, etc.) and halogen (e.g. fluorine, chlorine, bromine, iodine, etc.). These substituents may substitute on the aryl group at any possible positions, and two or more of such substituents may be the same or different. The number of these substituents is, for example, about 1 to 5, preferably 1 to 3.

The "optionally substituted lower alkyl" includes the "lower alkyl" and "its substituents" mentioned above. The preferable examples are a $C_{1-4}$ alkyl group (e.g. methyl, ethyl, propyl, isopropyl, etc.).

The substituent group by which said "amino" mentioned above may be substituted includes (i) lower alkyl (e.g. $C_{1-4}$ alkyl such as methyl, ethyl, n-propyl, i-propyl, etc.), (ii). lower alkyl-carbonyl (e.g. $C_{1-4}$ alkyl-carbonyl such as acetyl, propionyl, butyryl, etc.), (iii) lower alkoxy-carbonyl (e.g. $C_{1-4}$ alkoxy-carbonyl such as methoxycarbonyl, ethoxycarbonyl, propoxycarbonyl, etc.), (iv) halogen (e.g. fluorine, chlorine, bromine, etc.) and (v) phenyl which may be substituted by 1 to 5 substituent groups selected from the group consisting of halogen-(e.g. fluorine, chlorine, bromine, etc.), $C_{1-4}$, alkyl (e.g. methyl, ethyl, n-propyl, i-propyl, etc.) and $C_{1-4}$ alkoxy (e.g. methoxy, ethoxy, propoxy, etc.) such as phenyl, 4-chlorophenyl, 3-chlorophenyl, 2-chlorophenyl, 4-methylphenyl, 3-methylphenyl, 2-methylphenyl, 4-methoxyphenyl, 3-methoxyphenyl, 2-methoxyphenyl, etc.. The number of these substituents is, for example, 1 or 2. The preferable examples are a mono- or di-$C_{1-4}$ alkyl group (e.g. methylamino, ethylamino, dimethylamino, diethylamino, etc.)

The substituent group of said "optionally substituted" amido mentioned above includes said species of "optionally substituted lower alkyl" mentioned above. The preferable examples are an acetamido group.

The term "halogen" throughout this specification includes fluorine, chlorine, bromine and iodine.

The term "5- to 7-membered ring formed in combination with the adjacent —C=C— group" throughout this specification is a 5- to 7-membered ring which may contain 1 to 4 hetero-atoms selected from among, for example, a nitrogen atom, an oxygen atom, a sulfur atom in addition to carbon atoms. Thus, 5- to 7-membered hydrocarbon rings such as $C_{5-7}$ cycloalkene (e.g. cyclopentene, cyclohexene, cycloheptene, etc.), benzene, etc.; and 5- to 7-membered nitrogen-containing heterocyclic ring such as pyrrole, pyridine, piperidine, etc. can be mentioned as the common species.

The term "3- to 7-membered homocyclic ring" throughout this specification, may, for example, be a 3- to 7-membered homocyclic ring consisting exclusively of carbon atoms, i.e. 3- to 7-membered cyclic hydrocarbon. Thus, for example, $C_{3-7}$ cycloalkanes e.g. cyclopropane, cyclobutane, cyclopentane, cyclohexane, cycloheptane, etc.), $C_{3-7}$ cycloalkenes e.g. cyclopropene, cyclobutene, cyclopentene, cyclohexene, cycloheptene, etc.) and benzene can be mentioned as the common species.

The divalent group derived from said "3- to 7-membered homocyclic ring" throughout this specification means, for example, a divalent group obtainable by removing two hydrogen atoms which bond to one carbon atom in said 3- to 7-membered homocyclic ring or respectively removing one hydrogen atom which bonds to each of two different carbon atoms in said homocyclic ring such as the following:

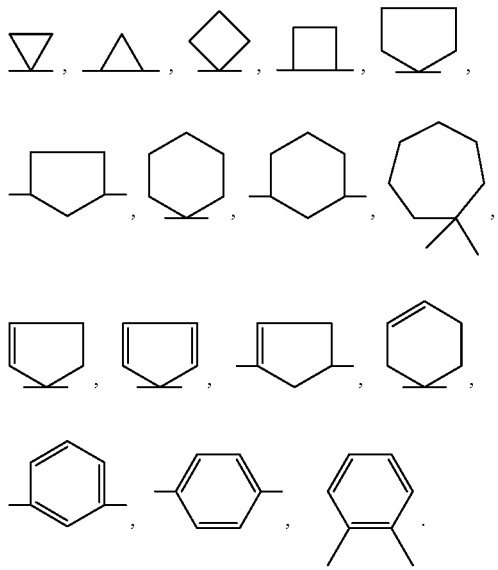

Particularly useful are $C_{3-7}$ cycloalkylidene groups such as the following:

The term "3- to 7-membered heterocyclic ring" throughout this specification is a 3- to 7-membered heterocyclic ring which may contain 1 to 4 hetero-atoms selected from among nitrogen, oxygen, sulfur and other atoms in addition to carbon atoms, for instance. Thus, for example, oxetane, tetrahydrofuran, tetrahydropyran, pyrrole, azetidine, pyrrolidine, piperidine, piperazine, tetrahydrothiophene, homopiperidine, morpholine, etc. can be employed.

The divalent group derived from said "3- to 7-membered heterocyclic ring" means a group resulting from either elimination of two hydrogen atoms from a single carbon atom in the 3- to 7-membered heterocyclic ring or elimination of one hydrogen atom from each of two different atoms therein. Thus, for example, the following groups can be included:

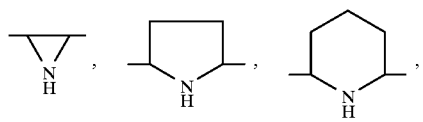

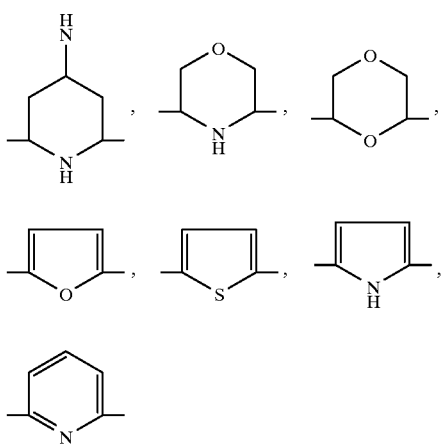

The term "cyclic amino" throughout this specification means a group resulting from elimination of one hydrogen atom from a nitrogen atom in a ring such as a 3- to 13-membered nitrogen-containing heterocyclic ring which contains one nitrogen atom in addition to carbon atoms and which may also contain one to four hetero atoms, for example, selected from nitrogen, oxygen, sulfur and other atoms. Thus, for example, the following groups can be included:

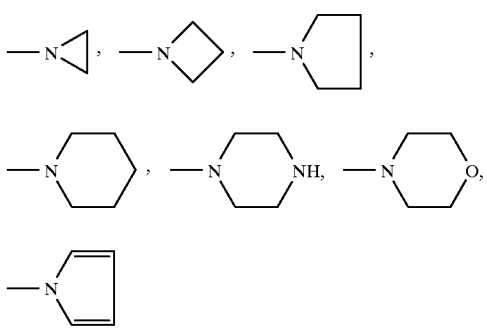

A preferable example of the "cyclic amino" is a 3- to to 9-membered cyclic amino group, such as

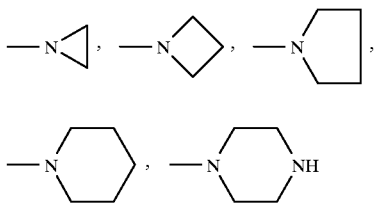

The substituent group by which said "3- to 7-membered homocycic ring", "3- to 7-membered heterocyclic ring" or "cyclic amino" may be substituted include, among others, optionally substituted lower alkyl (preferably, a $C_{1-4}$ alkyl group such as methyl, ethyl, etc.); optionally substituted amino (preferably, a mono- or di- $C_{1-4}$ alkylamino group such as methylamino, ethylamino, dimethylamino, diethylamino, etc.); hydroxy; carboxyl; nitro; lower alkoxy (e.g. $C_{1-6}$ alkoxy such as methoxy, ethoxy, propoxy, etc.); 5- to 7-membered nitrogen-containing heterocyclic group (e.g. pyrrolyl, imidazolyl, pyridyl or pyrimidyl, which may be substituted by 1 to 4 substituents selected from e.g. $C_{1-4}$ alkyl such as methy, ethyl, propyl, etc.) and halogen (e.g. fluorine, chlorine, bromine, iodine, etc.). These substituents may substitute on the ring at any possible position, and two or more of such substituents may be the same or different. The number of these substituents is, for example, about 1 to 5, preferably 1 to 3.

The substituent group for said "optionally substituted lower alkyl" and "optionally substituted amino" includes the same groups as the substitutents mentioned above in "lower alkyl" and "amino".

Referring to the general formulas presented hereinabove, $R^1$ represents a hydrogen atom, an optionally substituted lower alkyl group or a halogen atom. $R^1$ is preferably a hydrogen atom or a $C_{1-4}$ alkyl group (e.g. methyl, ethyl, n-propyl, i-propyl, etc.) and is more preferably a hydrogen atom.

$R^2$ and $R^3$ each represent a hydrogen atom or an optionally substituted lower alkyl group, or $R^2$ and $R^3$ may, taken together with the adjacent —C=C—, form a 5- to 7-membered ring. $R^2$ and $R^3$ independently are preferably hydrogen or a $C_{1-4}$ alkyl (e.g. methyl, ethyl, n-propyl, i-propyl, etc.). Particularly preferred is a combination of hydrogen for $R^2$ and a $C_{1-4}$ alkyl (e.g. methyl, ethyl, n-propyl, i-propyl, etc.) for $R^3$. Also preferred are cases in which $R^2$ and $R^3$ form a 5- to 7-membered carbocyclic ring in combination with the adjacent —C=C—. Particularly preferred is the case of cyclohexene, benzene or the like.

X stands for methylene, an oxygen atom or $S(O)_p$ (p is an integer of 0 to 2, preferably 1). X is a preferably an oxygen atom or a sulfur atom and more advantageously an oxygen atom.

Either A or B represents a nitrogen atom with the other representing a methine group, or both of A and B represent a methine group. Preferred is a combination of methine for A and nitrogen atom for B, or a combination of methine for both of A and B.

Y represents (i) a group of the formula:

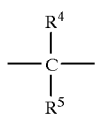

wherein $R^4$ and $R^5$ independently means a hydrogen atom or an optionally substituted lower alkyl group or (ii) a divalent group derived from an optionally substituted 3- to 7-membered homocyclic or heterocyclic ring.

A preferred example of Y is a group of the formula:

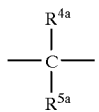

wherein $R^{4a}$ and $R^{5a}$ independently mean a hydrogen atom or a $C_{1-4}$ alkyl group such as methyl, ethyl, n-propyl, i-propyl, etc. Preferable examples of $R^{4a}$ and $R^{5a}$ include $C_{1-4}$ alkyl such as methyl, ethyl, n-propyl, i-propyl and so on.

Another preferred examples of Y are a $C_{3-7}$ cycloalkylidene group such as the following:

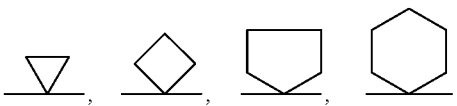

$R^6$ represents a primary to tertiary amino group.

The primary to tertiary amino group may, for example, be (i) an amino group which may be substituted by 1 or 2 substituent groups selected from the group consisting of an optionally substituted lower alkyl group, an optionally substituted cycloalkyl group and an optionally substituted aryl group, or (ii) an optionally substituted cyclic amino group. Particularly preferred is a group of the formula

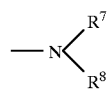

In the above formula, $R^7$ and $R^8$ independently are (i) a hydrogen atom, (ii) a $C_{1-4}$ alkyl group which may be substituted by one pyrrolyl, imidazolyl, pyridyl or pyrimidyl group which may in turn be substituted by one $C_{1-4}$ alkyl group (e.g. methyl, ethyl, n-propyl, i-propyl, etc.), such as 2-(1-methylpyrrol-2-yl)ethyl, (1-methylimidazolyl)ethyl, etc., or (iii) a $C_{3-6}$ cycloalkyl group (e.g. cyclopropyl, cyclobutyl, cyclopentyl, cyclohexyl, etc.). Groups of the following formula are further preferred examples of $R^6$.

In the above formula, $R^9$ represents a hydrogen atom, an optionally substituted lower alkyl group or an optionally substituted heterocyclic group. Preferred examples of $R^9$ are hydrogen, $C_{1-4}$ alkyl (e.g. methyl, ethyl, n-propyl, i-propyl, etc.) and pyrimidyl. The most useful example of $R^6$ is an amino group.

The symbol m represents an integer of 0 to 4. Preferably, m is 1 to 4, and for still better results, m is 1. The symbol n represents an integer of 0 to 4. Preferably n is 1 to 4. The most desirable is a combination of 1 for m and 1 to 4 for n.

The compound [I] or salt thereof can be produced by the per se known processes or processes analogous thereto. For example, the processes described in EP-A-185346, EP-A440119, EP-A-444549, EP-A-548923, etc. can be used.

(A): The compound [I] or a salt thereof can be produced by reacting a compound of the general formula

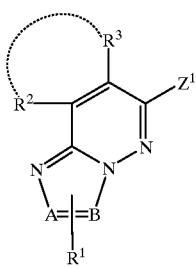

[II]

wherein $Z^1$ represents a reactive group; the other symbols have the same meanings defined hereinbefore or a salt thereof with a compound of the general formula:

$$Z^2X—(CH_2)_m—Y—(CH_2)_n—SO_2—R^6 \qquad [III]$$

wherein $Z^2$ represents a group which leaves on reacting with $Z^1$; the other symbols have the same meanings defined hereinbefore or a salt thereof.

The reactive group represented by $Z^1$ may for example be a halogen atom (e.g. chlorine, bromine, iodine, etc.), a $C_{6-10}$ arylsulfonyloxy group (e.g. benzenesulfonyloxy, p-tolylsulfonyloxy, etc.) or a $C_{1-4}$ alkanesulfonyloxy group (e.g. methanesulfonyloxy).

The group which leaves on reacting with $Z^1$ represented by $Z^2$ may for example be a hydrogen atom or an alkali metal (e.g. sodium, potassium, etc.), where X represents an oxygen or sulfur atom, or an alkali metal (e.g. sodium, potassium, etc.), where X represents —SO— or —SO$_2$—.

In this reaction, the compound (III) or a salt thereof is used in a proportion of generally 1 to 5 moles and preferably 1 to 2 moles per mole of the compound (II) or a salt thereof.

This condensation reaction is preferably carried out in the presence of a base. Examples of the base include e.g. an alkali metal hydride such as sodium hydride, potassium hydride, etc.; an alkali metal alkoxide such as sodium methoxide, sodium ethoxide, etc.; an alkali metal hydroxide such as sodium hydroxide, potassium hydroxide, etc.; or a carbonate such as sodium carbonate, potassium carbonate and so on.

Furthermore, this reaction can be carried out in an inert solvent, e.g. alcohols such as methanol, ethanol, etc.; ethers such as dioxane, tetrahydrofuran, etc.; aromatic hydrocarbons such as benzene, toluene, xylene, etc.; nitriles such as acetonitrile etc.; amides such as dimethylformamide, dimethylacetamide, etc.; and sulfoxides such as dimethyl sulfoxide and so on.

The reaction temperature is generally 10 to 200° C. and preferably 50 to 100° C. The reaction time is generally 0.5 to 24 hours and preferably 1 to 6 hours. (B): The compound [I] or a salt thereof can also be produced by reacting a compound of the general formula

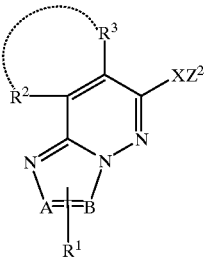

[IV]

wherein all symbols have the same meanings defined hereinbefore or a salt thereof with a compound of the general formula:

$$Z^1—(CH_2)_m—Y—(CH_2)_n—SO_2—R^6 \qquad [V]$$

wherein all symbols have the meanings defined hereinbefore or a salt thereof.

In this reaction, the compound (V) or a salt thereof is used in a proportion of generally 1 to 5 moles and preferably 1 to 2 moles per mole of compound (IV) or a salt thereof.

This condensation reaction is preferably carried out in the presence of a base. The base that can be used includes alkali metal hydrides such as sodium hydride, potassium hydride etc.; alkali metal alkoxides such as sodium methoxide, sodium ethoxide, etc.; alkali metal hydroxides such as sodium hydroxide, potassium hydroxide, etc.; and carbonates such as sodium carbonate, potassium carbonate, etc.; among other bases.

Furthermore, this reaction can be carried out in an inert solvent, e.g. alcohols such as methanol, ethanol, etc.; ethers such as dioxane, tetrahydrofuran, etc.; aromatic hydrocarbons such as benzene, toluene, xylene, etc.; nitriles such as acetonitrile etc.; amides such as dimethylformamide, dimethylacetamide, etc.; and sulfoxides such as dimethyl sulfoxide and the like.

The reaction temperature is generally 10 to 200° C. and preferably 50 to 150° C. The reaction time is generally 0.5 to 24 hours and preferably 1 to 10 hours. (C): The compound [I] or a salt thereof can also be produced by reacting a compound of the general formula:

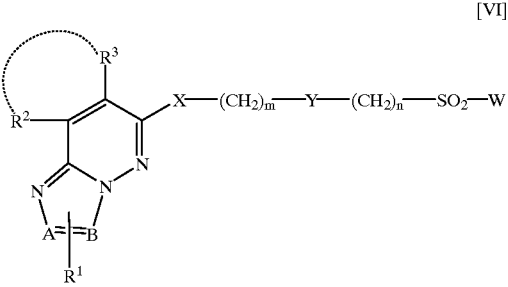

[VI]

wherein W means a leaving group; the other symbols have the same meanings defined hereinbefore or a salt thereof with a compound of the general formula:

$$R^6—H \qquad [VII]$$

wherein $R^6$ is as defined hereinbefore or a salt thereof.

The leaving group represented by W may for example be a halogen atom (e.g. chlorine, bromine, iodine, etc.), a $C_{6-10}$ arylsulfonyloxy group (e.g. benzenesulfonyloxy, p-tolylsulfonyloxy, etc.), a $C_{1-4}$ alkanesulfonyloxy group (e.g. methanesulfonyloxy etc.). Particularly preferred is a halogen atom (e.g. chlorine, bromine, iodine, etc.).

In this reaction, the compound (VII) or a salt thereof is used in a proportion of generally 1 to 5 moles and preferably 1 to 2 moles per mole of compound (VI) or a salt thereof.

This reaction can be carried out in an inert solvent, e.g. alcohols such as methanol, ethanol, etc., ethers such as dioxane, tetrahydrofuran, etc., aromatic hydrocarbons such as benzene, toluene, xylene, etc., nitrites such as acetonitrile etc., amides such as dimethylformamide, dimethylacetamide, etc., and sulfoxides such as dimethyl sulfoxide and the like.

The reaction temperature is generally −20 to 100° C. and preferably −10 to 50° C. The reaction time is generally 0.5 to 5 hours and preferably 1 to 3 hours.

When the product compound obtained by any of said processes (A), (B) and (C) is a free compound, it can be converted to a salt in the per se known manner. And, when the product compound is a salt, it can be converted to the free compound or a different kind of salt in the per se known manner. The compound [I] or salt thus obtained can be isolated and purified by the known procedures such as solvent extraction, pH adjustment, redistribution, precipitation, crystallization, recrystallization and chromatography and so on. Where said compound [I] or a salt thereof is a mixture of optically active compounds, it can be resolved into the d- and l-forms by the conventional optical resolution technique.

The method of producing for the starting compounds [II], [III], [IV], [V], [VI], and [VII], as well as salts thereof, which are used in the production of compound [I] and its salts of the present invention are described.

Incidentally, the salts of these compounds can be salts with inorganic acids (e.g. hydrochloric acid, phosphoric acid, hydrobromic acid, sulfuric acid, etc.) or salts with organic acids (e.g. acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.). Furthermore, where these compounds have acidic groups such as —COOH, they may form salts with inorganic bases (e.g. alkali or alkaline earth metals such as sodium, potassium, calcium, magnesium, etc., ammonia and so on) or organic bases (e.g. tri-$C_{1-3}$ alkylamine such as triethylamine etc.).

The starting compound [II] or a salt thereof can be synthesized by e.g. the process described in J. Org. Chem. 39, 2143, 1987 or any process analogous thereto.

The starting compound [III] or a salt thereof and the compound [V] or a salt thereof can be synthesized by e.g. the processes described in Chem. Ber. 91, 2130, 1958, J. Org. Chem. 52, 2162, 1987 and Japanese Tokkyo Kokai Koho H3-223287 or processes analogous thereto.

The starting compound [IV] or a salt thereof can be produced by e.g. the process described in Japanese Tokkyo Kokai Koho H3-223287 or any analogous process.

The starting compound [VI] or a salt thereof can be synthesized by (1) reacting a compound [II] or a salt thereof with a compound of the formula:

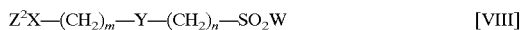

$$Z^2X—(CH_2)_m—Y—(CH_2)_n—SO_2W \qquad [VIII]$$

wherein all symbols have the same meanings defined hereinbefore or (2) reacting a compound [IV] or a salt thereof with a compound of the formula:

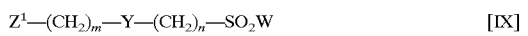

$$Z^1—(CH_2)_m—Y—(CH_2)_n—SO_2W \qquad [IX]$$

wherein all symbols have the same meanings defined hereinbefore.

In the above reaction (1), the compound [VIII] or a salt thereof is used in a proportion of generally 1 to 5 moles and preferably 1 to 2 moles per mole of the compound [II] or a salt thereof. This reaction can be conducted in the same manner as the above-mentioned reaction between compound [II] or a salt thereof and compound [III] or a salt thereof.

In the above reaction (2), the compound [IX] or a salt thereof is used in a proportion of generally 1 to 5 moles and preferably 1 to 2 moles per mole of the compound [IV] or a salt thereof. This reaction can be conducted in the same manner as the above-mentioned reaction between compound [IV] or a salt thereof and compound [V] or a salt thereof.

The starting compound [VII] or a salt thereof, the starting compound [VIII] or a salt thereof, and the starting compound [IX] or a salt thereof can all be produced by per se known processes or any processes analogous thereto.

The starting compounds and salts thus produced can be isolated by the known procedures such as solvent extraction, pH adjustment, redistribution, precipitation, crystallization, recrystallization, chromatography, etc. The reaction mixture containing the particular compound or salt may be directly submitted to the next reaction.

(D): Alternatively, the compound [I] wherein X is methylene, or a salt thereof, can be produced by reacting a compound of the formula:

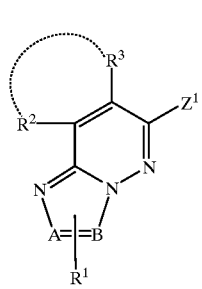

[II]

wherein all symbols have the same meanings defined hereinbefore or a salt thereof with a compound of the formula:

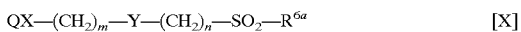

$$QX—(CH_2)_m—Y—(CH_2)_n—SO_2—R^{6a} \qquad [X]$$

wherein Q represents a group which can leave on reacting with $Z^1$; $R^{6a}$ represents an optionally protected amino group; the other symbols have the same meanings defined hereinbefore or a salt thereof.

Q represents a group which can leave on reacting with $Z^1$. To be specific, the group represented by $Z^1$ includes halogen. (e.g. chlorine, bromine, iodine, etc.), $C_{6-10}$ arylsulfonyloxy (e.g. benzenesulfonyloxy, p-tolylsulfonyloxy, etc.) and $C_{1-4}$ alkanesulfonyloxy (e.g. methanesulfonyloxy, trifluoromethanesulfonyloxy, etc.), among others. The group represented by Q may for example be a metal halide, of which the halide ion (e.g. chlorine, bromine and iodine) is preferably iodine and the metal (e.g. zinc, magnesium, etc.) is preferably zinc.

This condensation reaction is preferably carried out in the presence of a palladium catalyst. The term "palladium catalyst" is used herein to mean any catalyst that can be used for palladium catalyst-cross coupling reactions as described in Accounts of Chemical Research 12, 146–151, 1979; ditto 15, 340–348, 1982; Angew. Chem. Int. Ed. Engl. 25, 508–524, 1986, etc., thus including a palladium-tertiary phosphine complex system or a palladium salt or palladium complex-tertiary phosphine system. The palladium-tertiary phosphine complex system is a complex of palladium (0 or II) with a tertiary phosphine such as trialkylphosphines, triarylphosphines, etc., thus including tetrakis (triphenylphosphine)palladium, bis-(triphenylphosphine) palladium bromide, bis(triphenyl-phosphine)palladium chloride, acetoxybis(triphenyl-phosphine)palladium, benzylchlorobis(triphenylphosphine)palladium, tetra-kis (tributylphosphine)palladium, bis(tri-methylphosphine) palladium chloride, bis(triethylphosphine)palladium chloride, bis(tripropylphosphine)palladium chloride, bis (tributylphosphine)palladium chloride and so on. Preferred are tetrakis(triphenylphosphine)palladium, bis (triphenylphosphine)palladium bromide, bis (triphenylphosphine)palladium chloride, acetoxybis (triphenylphosphine)palladium and so on.

The palladium salt mentioned above is a salt between a divalent palladium ion and an acid residue, such as palladium chloride, palladium bromide, palladium acetate, palladium nitrate, palladium sulfate and so on. Preferred are palladium chloride, palladium bromide and palladium acetate.

The palladium complex includes not only said palladium-tertiary phosphine complexes but also other complex compounds of palladium (0 or II), thus including bis (phenylethylamine)palladium chloride, bis(benzonitrile) palladium chloride, bis(benzonitrile)palladium bromide, bis-(acetonitrile)palladium chloride and so on. Preferred are bis(benzonitrile)palladium chloride, bis(acetonitrile) palladium chloride and so on.

The tertiary phosphine may for example be triphenylphoshine, tributylphosphine, tripropylphosphine, triethylphosphine or trimethylphosphine. A preferred example is triphenylphosphine.

This reaction is preferably carried out in a solvent. The solvent that can be used includes aromatic hydrocarbons such as benzene, toluene, xylene, etc.; ethers such as diethyl ether, tetrahydrofuran, dioxane, etc.; amides such as dimethylformamide, dimethylacetamide, etc.; sulfoxides such as dimethyl sulfoxide, and nitrites such as acetonitrile, among other solvents. The reaction temperature may range from 0° to 200° C. and is preferably 100 to 100° C. The reaction time may range from 30 minutes to 24 hours and is preferably 1 to 3 hours. This reaction can be conducted with advantage in a stream of nitrogen or argon gas. The reaction product can be separated and purified by the per se known procedures such as solvent extraction, pH adjustment, redistribution, precipitation, crystallization, recrystallization and chromatography.

In conducting this reaction, when $R^{6a}$ in general formula [X] is an amino group, this amino group is preferably protected using a protective group which is well known in the field of peptide chemistry. The protective group thus includes amide-forming protective groups such as formyl, acetyl, benzoyl, etc.; carbamate-forming protective groups such as tert-butoxycarbonyl, benzyloxycarbonyl, etc.; and imino-type protective groups such as dimethylaminomethylene, benzylidene, p-methoxybenzylidene, diphenylmethylene, and so on. Preferred protective groups are formyl, acetyl and dimethylaminomethylene. Where the reaction product has any protective group, the group can be removed by the conventional method, for example by hydrolysis with an acid or a base or by catalytic reduction.

Incidentally, the starting compound [X] or a salt thereof can be prepared by the per se known processes and analogous processes.

Referring to the reactions for synthesis of said compound [I] or a salt thereof or of its starting compounds, where any of the reactants has an amino, carboxyl and/or hydroxyl group as a substituent, such substituent group may have been protected with a protective group which is conventionally used in peptide chemistry. In such cases the desired compounds can be obtained by removing the protective groups after the respective reactions.

The protective group that can be used for the protection of such an amino group includes unsubstituted or substituted $C_{1-6}$ alkyl-carbonyl (e.g. formyl, acetyl, ethylcarbonyl, etc.), phenylcarbonyl, $C_{1-6}$ alkyl-oxycarbonyl (e.g. methoxycarbonyl, ethoxycarbonyl, etc.), phenyloxycarbonyl (e.g. benzoyl etc.), $C_{7-10}$ aralkyl-carbonyl (e.g. benzylcarbonyl etc.), trityl, phthaloyl and so on. The substituents that may be present on the above-mentioned groups may be halogen (e.g. fluorine, chlorine, bromine, iodine), $C_{1-6}$ alkyl-carbonyl (e.g. methylcarbonyl, ethylcarbonyl, butylcarbonyl, etc.), nitro and so on. The number of substituents may range from 1 to about 3.

The protective group that can be used for the protection of a carboxyl group includes unsubstituted or substituted $C_{1-6}$ alkyl (e.g. methyl, ethyl, n-propyl, i-propyl, n-butyl, tert-butyl, etc.), phenyl, trityl, silyl and so on. The substituents on such protective groups may be halogen (e.g. fluorine, chlorine, bromine, iodine), $C_{1-6}$ alkyl carbonyl (e.g. formyl, acetyl, ethylcarbonyl, butylcarbonyl, etc.), nitro and so on. The number of substituents may range from 1 to about 3.

The protective group that can be used for the protection of a hydroxyl group includes unsubstituted or substituted $C_{1-6}$ alkyl (e.g. methyl, ethyl, n-propyl, i-propyl, n-butyl, tert-butyl, etc.), phenyl, $C_{7-10}$ aralkyl (e.g. benzyl), $C_{1-6}$ alkyl-carbonyl (e.g. formyl, acetyl, ethylcarbonyl, etc.), phenyloxycarbonyl (benzoyl), $C_{7-10}$ aralkyl-carbonyl (e.g. benzylcarbonyl), pyranyl, furanyl, silyl and so on. The substituent or substituents on such protective groups may be halogen (e.g. fluorine, chlorine, bromine, iodine), $C_{1-6}$ alkyl, phenyl, $C_{7-10}$ aralkyl (e.g. benzyl), nitro and so on. The number of substituents may range from 1 to about 4.

The procedure for eliminating such protective groups may be any known procedure or a procedure analogous thereto and includes processes involving the use of an acid or a base, reduction, UV irradiation, and processes employing hydrazine, phenylhydrazine, sodium N-methyldithiocarbamate, tetrabutylammonium fluoride, palladium acetate or other reagent, among other procedures.

The salt of compound [I] according to this invention is preferably a physiologically acceptable acid addition salt. The salt of this type includes salts with inorganic acids (e.g. hydrochloric acid, phosphoric acid, hydrobromic acid, sulfuric acid, etc.) and salts with organic acids (e.g. acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.). Where the compound [I] of this invention has an acidic group such as —COOH, the compound [I] may form salts with inorganic bases (e.g. alkali metals and alkaline earth metals such as sodium, potassium, calcium, magnesium, etc., and ammonium) and salts with organic bases (e.g. tri-$C_{1-3}$ alkylamines such as triethylamine).

The compound of formula [I] and a salt thereof have an excellent eosinophil chemotaxis inhibitory activity and can be used with advantage and safety in mammalian animals (e.g. man, mouse, dog, rat, bovine, etc.), particularly for the treatment of allergic rhinitis, atopic dermatitis and so on. Although the compound [I] or a salt thereof in the present invention may be used as such in the bulk form, it can be administered in the form of a pharmaceutically acceptable preparation which can be prepared using appropriate amounts of the conventional formulation additives selected from among various excipients (e.g. calcium carbonate, kaolin, sodium hydrogen carbonate, lactose, starch, crystalline cellulose, talc, granulated sugar, porous matrices, etc.), binders (e.g. dextrin, natural gum, gelatinized starch, gelatin, hydroxypropylcellulose, hydroxypropylmethylcellulose, pullulan, etc), disintegrators (e.g. carboxymethylcellulose sodium, croscarmellose sodium, crospovidone, low-substitution-degree hydroxypropylcellulose, partially gelatinized starch, etc.), lubricants (e.g. magnesium stearate, calcium stearate, talc, starch, sodium benzoate, etc.), coloring agents (e.g. tar color, caramel, iron sesqui-oxide, titanium dioxide, riboflavine, etc.), corrigents (e.g. sweeteners, perfumes, etc.), stabilizers (e.g. sodium sulfite etc.) and preservatives (e.g. parabens, sorbic acid, etc.) in the per se known manner. The pharmaceutical composition of this invention contains a therapeutically or prophylactically effective amount of said compound [I] or salt thereof. The proportion of compound [I] or a salt based on the total weight of the pharmaceutical composition of the invention is about 0.1 to 100 weight %.

The pharmaceutical composition of this invention may further contain, in addition to said compound [I] or a salt thereof, certain other medicinal substances (e.g. antiasthmatic agent, antiallergic agent, antiinflammatory agent, etc.). Such concomitant medicinal substances are not restricted in type insofar as the objects of this invention can be accomplished, and can be added in appropriated amounts. The dosage form which can be employed includes tablets (including dragees, film-coated tablets, etc.), pills, capsules, granules, fine granules, powders, syrups, emulsions, suspensions, injectable solutions, inhalants, ointments and so on. These dosage forms can be manufactured by the established pharmaceutical procedures (e.g. the procedures described in Japanese Pharmacopoeia).

Thus, tablets can be manufactured by adding a lubricant to a bulk powder of the active substance or a uniform mixture of the active substance with an excipient, binder, lubricant and/or other formulation additive and compression-molding the resulting composition. If required, a coloring agent, a corrigent and other auxiliary additive agent can be added. Moreover, tablets can be coated with a suitable coating composition.

Injections can be manufactured by dissolving, suspending or emulsifying a calculated amount of the active substance in water for injection, physiological saline, Ringer's solution or the like for an aqueous system or in a vegetable oil or equivalent for a non-aqueous system to provide unit dosage preparations or sealing it in vials or other containers for injection.

The carrier that can be used for peoral dosage forms includes starch, mannitol, crystalline cellulose, carboxymethylcellulose sodium and other substances which are generally used in pharmaceutical manufacture. The carrier or vehicle for injections includes distilled water, physiological saline, glucose solution, infusion fluids and so on. Aside from the substances mentioned above, those auxiliary additives which are generally used in pharmaceutical manufacture can also be added.

The active substance of this invention is a safe compound with a low toxic potential (acute toxicity: $LD_{50} > 2$ g/kg) which inhibits chemotaxis of eosinophils and, hence, local eosinophilic infiltration in allergic and inflammatory reactions. Therefore, this invention is useful for the treatment of diseases in which eosinophilic infiltration is involved. Thus, the pharmaceutical composition of this invention can be used in the therapy or prevention of various diseases involving eosinophilia in mammalian animals, for example, allergic diseases such as urticaria, atopic dermatitis, allergic rhinitis, hypersensitive pneumonia, etc., diseases of the skin such as eczema, dermatitis herpetiformis, psoriasis, etc., and respiratory diseases such as simple pulmonary eosinophilia (PIE syndrome).

The dosage of the pharmaceutical composition of this invention varies with the patient's age, body weight and condition, the route and frequency of administration and other factors. Taking an adult human weighting 60 kg as an example, 0.1 to 100 mg/kg/day, preferably 1 to 50 mg/kg/day, and for still better results, 1 to 10 mg/kg, all as compound [I] or salt thereof, can be administered in a few divided doses. The route of administration may be oral or parenteral.

The following test example and examples are merely intended to illustrate this invention in further detail and should by no means be construed as defining the scope of the invention.

TEST EXAMPLE 1

1) Preparation of a guinea pig eosinophil suspension

Male Hartley guinea pigs (body weights approx. 300 g) were intraperitoneally treated with 2 ml of horse serum (Whittaker Bioproducts) once a week for 8 consecutive weeks. Forty-eight (48) hours after the last treatment, 75 ml of physiological saline was infused into the peritoneal cavity and the lavage was collected and centrifuged at 400 G (1500 rpm) for 5 minutes. The pellet was suspended in 5 ml of Percoll discontinuous density, gradients (specific gravity d=1.07), layered on top of the Percoll suspensions (specific gravity d=1.112:5 ml, d=1.095:10 ml, d=1.090:10 ml, d=1.085:7 ml) and centrifuged (18° C.) at 1000 G (2200 rpm) for 30 minutes. The cell layer formed in the boundary zone between the d=1.112 and d=1.095 layers was collected. The collected cell sediment was subjected to hypotonic treatment (suspended in water for 30 seconds) to remove the contaminant erythrocytes.

The sediment was washed three times with Hanks solution containing 10 mM Hepes (Dojin Kagaku) (Hanks-Hepes) and suspended in Hanks-Hepes containing 2% (w/v) human serum albumin (Wako Pure Chemical) (Hanks-Hepes-HSA) at a concentration of $2 \times 10^6$ cells/ml. The eosinophil purity was 92–96% and the viability of eosinophils was not less than 98%.

2) Chemotaxis inhibition assay

A suspension of $LTB_4$ (Cascade Bioproducts Ltd.) in Hanks-Hepes-HSA, 100 μl, was put in the lower compartment of a blind well chamber and, after placement of a nitrocellulose filter (Sartorius, pore size 8 μm), 100 μl of the eosinophil suspension ($2 \times 10^5$ cells) was put in the upper compartment. After 2 hours of reaction in a carbon dioxide gas incubator at 37° C., the suspension in the upper compartment was discarded and the filter was dismounted, air-dried on slide glass and fixed with ethanol. The filter was stained with Chromotrope 2R and hematoxylin, made transparent with xylene and embedded in balsam. The cells which had chemotactically migrated to 10 μm from the underside of the filter were counted for 5 fields (high power fields) under a light microscope (400 x magnification). The drug was dissolved in DMSO (dimethyl sulfoxide) and added to both the upper and lower compartments of the chamber.

$$\text{Chemotaxis inhibition rate} = \left(1 - \frac{\text{Sum of chemotactic cells in the presence of the drug}}{\text{Sum of chemotactic cells in the absence of the drug}}\right) \times 100.$$

The test substance was prepared at a concentration of $1 \times 10^{-5}$ M and the chemotaxis inhibition rate was determined. The results are shown in Tables 1 and 2.

TABLE 1

Inhibitory effect on chemotaxis of guinea pig eosinophils

| Compound No. | $R^1$ | $R^{1a}$ | $R^2$ | $R^3$ | X | Y | m | n | $R^6$ | Chemotaxis Inhibition rate (%) $10^{-5}$ M |
|---|---|---|---|---|---|---|---|---|---|---|
| I-1 | H | H | H | H | S | $CH_2$ | 1 | 1 | $NH_2$ | 38 |
| I-2 | H | H | H | H | S | $CH_2$ | 1 | 1 | 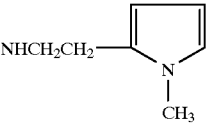 | 42 |
| I-3 | H | H | H | H | S | $CH_2$ | 1 | 1 | 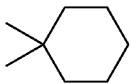 | 47 |
| I-4 | H | H | H | H | O | $CH_3$ | 1 | 1 | $NH_2$ | 47 |
| I-5 | H | H | H | H | O | 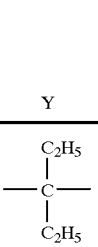 | 1 | 1 | $NH_2$ | 37 |

TABLE 2

Inhibitory effect on chemotaxis of guinea pig eosinophils

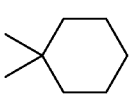

| Compound No. | A | B | $R^2$ | $R^3$ | X | Y | m | n | $R^6$ | Chemotaxis inhibition rate (%) $10^{-5}$ M |
|---|---|---|---|---|---|---|---|---|---|---|
| II-1 | CH | N | H | $CH_3$ | O | $\begin{array}{c} C_2H_5 \\ \mid \\ -C- \\ \mid \\ C_2H_5 \end{array}$ | 1 | 1 | $NH_2$ | 57 |
| II-2 | CH | N | H | $CH_3$ | O | (1,1-dimethylcyclohexyl) | 1 | 1 | $NH_2$ | 31 |

It is apparent from Tables 1 and 2 that the compound [I] and its salt have potent inhibitory activity against eosinophil chemotaxis. The compound Nos. shown in Tables 1 and 2 are duplicated in the following examples.

EXAMPLE 1

| (1) Compound No. II-1 | 10.0 mg |
|---|---|
| (2) Lactose | 60.0 mg |
| (3) Corn starch | 35.0 mg |
| (4) Gelatin | 3.0 mg |
| (5) Magnesium stearate | 2.0 mg |

Using 0.03 ml of a 10% aqueous solution of gelatin (3.0 mg as gelatin), a mixture of 10.0 mg of compound No. II-1, 60.0 mg of lactose and 35.0 mg of corn starch was granulated through a 1 mm mesh sieve to obtain granules. The granules were dried at 40° C. and screened again. The resulting granules were mixed with 2.0 mg of magnesium stearate, and the mixture were compressed. The resulting core tablets were sugar-coated with an aqueous suspension containing sucrose, titanium dioxide, talc and gum arabic. The resulting tablets were grazed with beeswax to provide coated tablets.

EXAMPLE 2

| (1) Compound No. II-1 | 10.0 mg |
|---|---|
| (2) Lactose | 70.0 mg |
| (3) Corn starch | 50.0 mg |
| (4) Soluble starch | 7.0 mg |
| (5) Magnesium stearate | 3.0 mg |

Using 0.07 ml of an aqueous solution of soluble starch (7.0 mg as soluble starch), a mixture of 10.0 mg of compound No. II-1 and 3.0 mg of magnesium stearate was granulated. The granules were dried and blended with 70.0 mg of lactose and 50.0 mg of corn starch. The resultant composition was compressed to provide tablets.

EXAMPLE 3

| (1) Compound No. II-1 | 5.0 mg |
|---|---|
| (2) Sodium chloride | 20.0 mg |
| (3) Distilled water | To make 2 ml |

5.0 mg of compound No. II-1 and 20.0 mg of sodium chloride were dissolved in distilled water, to which distilled water was added up to the total volume of 2.0 ml. The resulting solution was filtered and filled into 2 ml-ampules under a sterile condition. The filled ampules were sterilized and sealed to provide an injection solution.

The pharmaceutical composition containing compound [I] or a salt thereof according to this invention exhibits excellent eosinophil chemotaxis inhibiting activity and is of value for the treatment of allergic diseases such as allergic rhinitis and atopic dermatitis.

What is claimed is:

1. A method for inhibiting eosinophil infiltration by administrating to a subject in need thereof an effective amount of a compound of the formula:

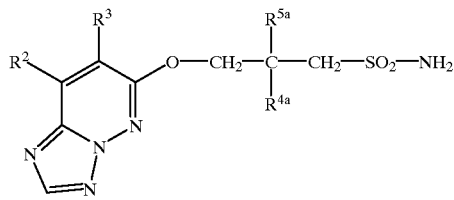

Wherein $R^2$ and $R^3$ independently represent a hydrogen atom or a $C_{1-4}$ alkyl group, and $R^{4a}$ and $R^{5a}$ independently represent a hydrogen atom or a $C_{1-4}$ alkyl group, or a pharmaceutically acceptable salt thereof.

2. A method according to claim 1, wherein $R^2$ is a hydrogen atom.

3. A method for treating an atopic dermatitis which comprises administrating to a subject in need thereof an effective amount of a compound of the formula:

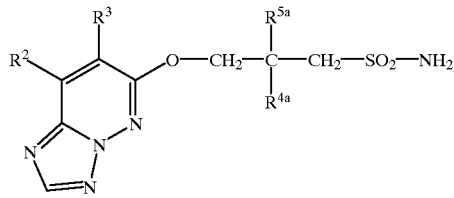

wherein $R^2$ and $R^3$ independently represent a hydrogen atom or a $C_{1-4}$ alkyl group, and $R^{4a}$ and $R^{5a}$ independently represent a hydrogen atom or a $C_{1-4}$ alkyl group, or a pharmaceutically acceptable salt thereof.

4. A method according to claim 3, wherein $R^2$ is a hydrogen atom.

* * * * *